(12) United States Patent
Gilfillan et al.

(10) Patent No.: US 8,299,091 B2
(45) Date of Patent: Oct. 30, 2012

(54) AMINOISOQUINOLINE THROMBIN INHIBITOR WITH IMPROVED BIOAVAILABILITY

(75) Inventors: Robert Gilfillan, Newhouse (GB); David Jonathan Bennett, Newhouse (GB)

(73) Assignee: MSD Oss B.V., Oss (NL)

( * ) Notice: Subject to any disclaimer, the term of this patent is extended or adjusted under 35 U.S.C. 154(b) by 343 days.

(21) Appl. No.: 12/376,529

(22) PCT Filed: Aug. 6, 2007

(86) PCT No.: PCT/EP2007/058111
§ 371 (c)(1), (2), (4) Date: Aug. 17, 2010

(87) PCT Pub. No.: WO2008/017650
PCT Pub. Date: Feb. 14, 2008

(65) Prior Publication Data
US 2010/0305153 A1  Dec. 2, 2010

(30) Foreign Application Priority Data
Aug. 8, 2006  (EP) .................................. 06118608

(51) Int. Cl.
*A61K 31/47* (2006.01)
*C07D 217/14* (2006.01)

(52) U.S. Cl. ........ 514/310; 514/307; 514/299; 514/279; 514/277; 546/143; 546/139; 546/112; 546/26

(58) Field of Classification Search ........................ None
See application file for complete search history.

(56) References Cited

U.S. PATENT DOCUMENTS

| | | | | |
|---|---|---|---|---|
| 5,457,114 | A | * | 10/1995 | Stuber et al. ................... 514/319 |
| 5,750,520 | A | * | 5/1998 | Danilewicz et al. ...... 514/217.07 |
| 6,194,409 | B1 | * | 2/2001 | van Boeckel et al. ........ 514/243 |

FOREIGN PATENT DOCUMENTS

| | | |
|---|---|---|
| WO | WO98/47876 | 10/1998 |
| WO | WO00/24718 | 5/2000 |

OTHER PUBLICATIONS

International Search Report for PCT/EP2007/058111; Performed by European Patent Office; Completed: Oct. 15, 2007; By authorized Officer Martin Fritz.

* cited by examiner

*Primary Examiner* — Timothy Thomas
*Assistant Examiner* — Theodore R West
(74) *Attorney, Agent, or Firm* — Richard S. Parr; Catherine D. Fitch

(57) ABSTRACT

The invention relates to the compound N-(2-oxo-2-propoxyethyl)-β-phenyl-D-phenyl-alanyl-N-[(1-amino-6-iso-quinolinyl)methyl]-L-prolinamide or a pharmaceutically acceptable salt thereof, to a pharmaceutical composition comprising said compound, as well as to the use of the compound for the manufacture of a medicament for treating or for preventing thrombin mediated diseases.

5 Claims, No Drawings

AMINOISOQUINOLINE THROMBIN INHIBITOR WITH IMPROVED BIOAVAILABILITY

CROSS REFERENCE TO RELATED APPLICATION

This application claims priority based on International Patent Application No. PCT/EP2007/058111, filed on Aug. 6, 2007.

FIELD OF THE INVENTION

The invention relates to a thrombin inhibitor comprising an aminoisoquinoline group, a pharmaceutical composition containing the same, as well as to the use of said inhibitor for the manufacture of a medicament for treating and preventing thrombin mediated diseases.

BACKGROUND OF THE INVENTION

The majority of peptide like thrombin inhibitors that have been reported in the literature contain a basic group in the so called $P_1$-position (R. Pfau, "*Structure-based design of thrombin inhibitors*", Current Opinion in Drug Discovery & Development, 6, 437-450, 2003). Examples of such basic groups include the basic amino acids arginine and lysine, and also guanidines and benzamidines. The basic moiety in these compounds is considered to be essential for antithrombotic activity. However, such highly basic groups are generally protonated at physiological pH and as a consequence such compounds are poorly absorbed across the gastrointestinal tract after oral dosing and have low oral bioavailability.

Therapeutic agents that may be given orally are, in general, greatly preferred and have enhanced commercial potential because of their inherent ease of use.

In the International Patent Application WO 98/47876 (Akzo Nobel N.V.) a class of thrombin inhibitors is disclosed having an aminoisoquinoline moiety as a basic group and these compounds have improved transepithelial transport properties. In particular this patent application exemplifies the compounds N-(carboxymethyl)-D-phenylalanyl-[(1-amino-6-isoquinolinyl)methyl]-L-prolinamide (WO98/47876: example 77) and N-(carboxymethyl)-D-(4-methoxyphenyl)alanyl-[(1-amino-6-isoquinolinyl)methyl]-L-prolinamide (WO98/47876: example 111as), as well as prodrug ester derivatives thereof.

It is desirable to develop more highly available thrombin inhibitors, particularly those suitable for oral administration.

DETAILED DESCRIPTION OF THE INVENTION

The present invention concerns the novel compound N-(2-oxo-2-propoxyethyl)-β-phenyl-D-phenylalanyl-N-[(1-amino-6-isoquinolinyl)methyl]-L-prolinamide, which is highly bio-available by oral administration.

In another aspect the invention concerns a pharmaceutical formulation comprising N-(2-oxo-2-propoxyethyl)-β-phenyl-D-phenylalanyl-N-[(1-amino-6-isoquinolinyl)methyl]-L-prolinamide, or a pharmaceutically acceptable salt thereof, in combination with a carrier or diluent.

A further aspect of the invention concerns the compound N-(carboxymethyl)-β-phenyl-D-phenylalanyl-N-[(1-amino-6-isoquinolinyl)methyl]-L-prolinamide, which is the selective thrombin inhibitor that is generated in situ from N-(2-oxo-2-propoxyethyl)-β-phenyl-D-phenylalanyl-N-[(1-amino-6-isoquinolinyl)methyl]-L-prolinamide following oral administration, and which is of use as an intermediate in the synthesis of the n-propyl-prodrug derivative of the invention.

The compound of the invention N-(2-oxo-2-propoxyethyl)-β-phenyl-D-phenylalanyl-N-[(1-amino-6-isoquinolinyl)methyl]-L-prolinamide is represented by structural Formula IA:

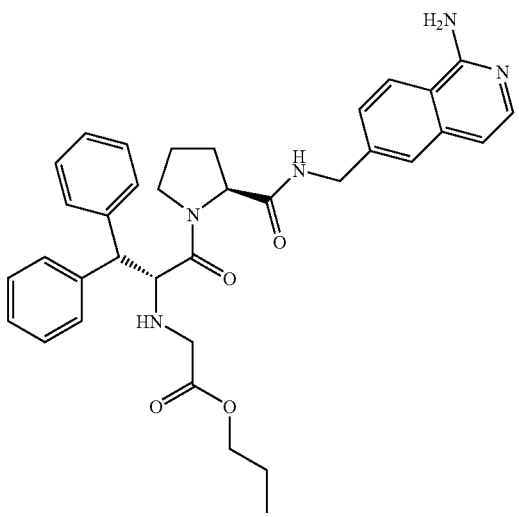

Formula 1A

It is a discovery of the present invention that the n-propyl-ester derivative 1A is highly bioavailable upon oral administration as compared to the bioavailability of the corresponding n-propyl ester derivatives of structurally closely related aminoisoquinoline thrombin inhibitors, such as N-(carboxymethyl)-D-phenylalanyl-[(1-amino-6-isoquinolinyl)methyl]-L-prolinamide (2A) and N-(carboxymethyl)-D-(4-methoxyphenyl)alanyl-[(1-amino-6-isoquinolinyl)methyl]-L-prolinamide (3A), disclosed in WO 98/4876. Thus, oral administration of the compound of the invention 1A results in remarkably high plasma concentrations of the thrombin inhibitor 1B, the free acid derivative of 1A, which is promptly generated in vivo once in the circulation.

The unexpectedly improved oral activity of the novel diphenylalanine derivative 1A in comparison with the corresponding phenylalanine derivative 2A or with the methoxyphenylalanine derivative 3A allows the development of an antithrombotic agent for oral administration at a relatively low dose.

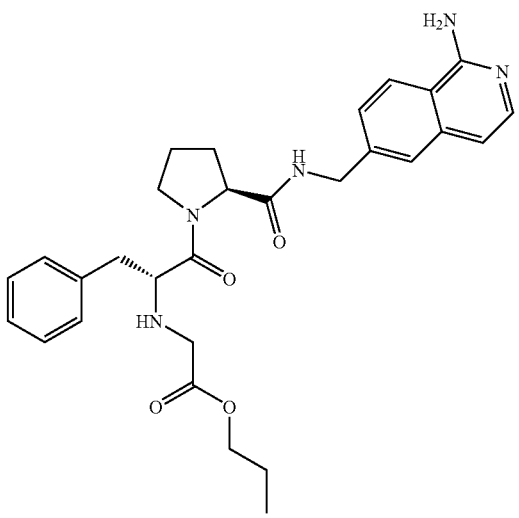

2A

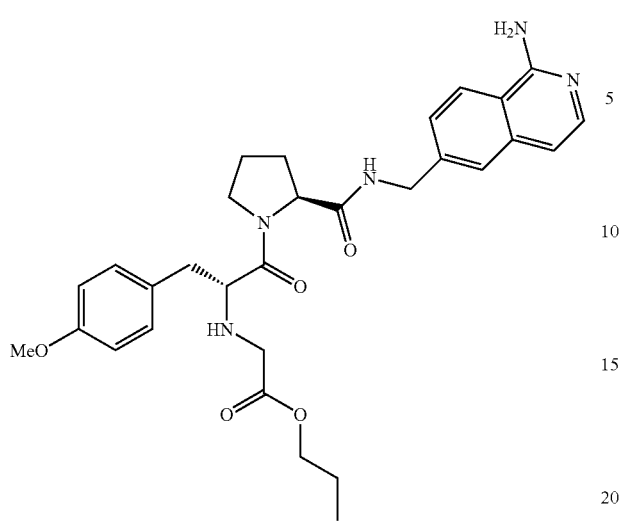

EXPERIMENTAL

General

LC-MS data were acquired on an Applied Biosystems API150EX mass spectrometer.

$^1$H NMR spectra were recorded on Bruker DPX 400 or DRX 400 spectrometers.

Example 1

Scheme I

N-(2-oxo-2-propoxyethyl)-β-phenyl-D-phenylalanyl-N-[(1-amino-6-isoquinolinyl)methyl]-L-prolinamide (1A)

A: N-[2-(1,1-Dimethylethoxy)-2-oxoethyl]-β-phenyl-D-phenylalanine (a)

To a stirred mixture of D-diphenylalanine, H-D-Dpa-OH, (20.0 g, 82.9 mmol) and potassium carbonate (17.2 g, 125 mmol) in dioxane/water (1:1 (v/v), 100 ml) was added tert-butyl bromoacetate (12.2 ml, 83.0 mmol). After stirring overnight water (100 ml) was added and the pH adjusted to 5.5 with 0.5M citric acid solution. The resultant precipitate was filtered off, washed with water then diethyl ether and dried under vacuum to give 10.4 g of the title compound a.

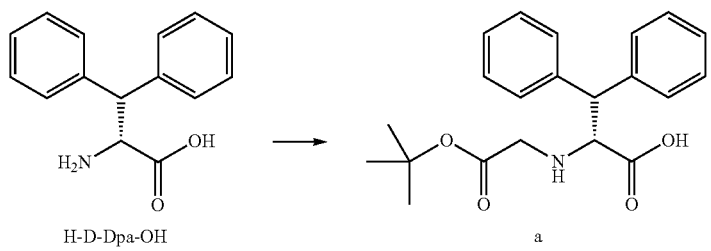

Scheme I.

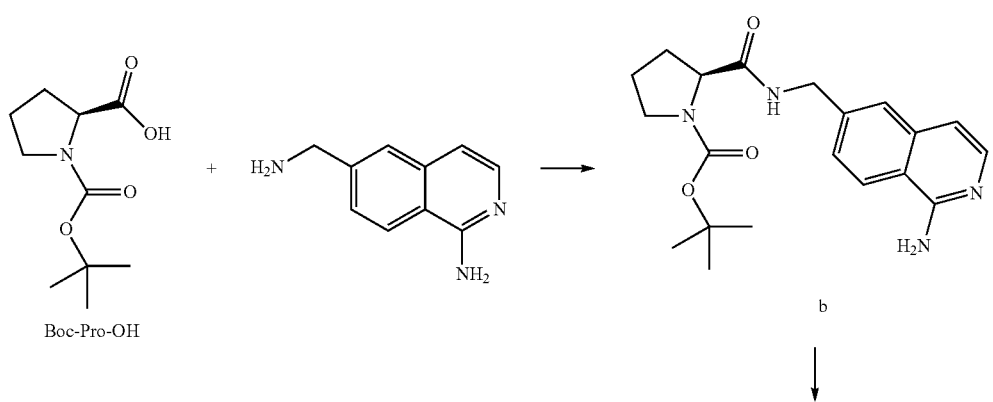

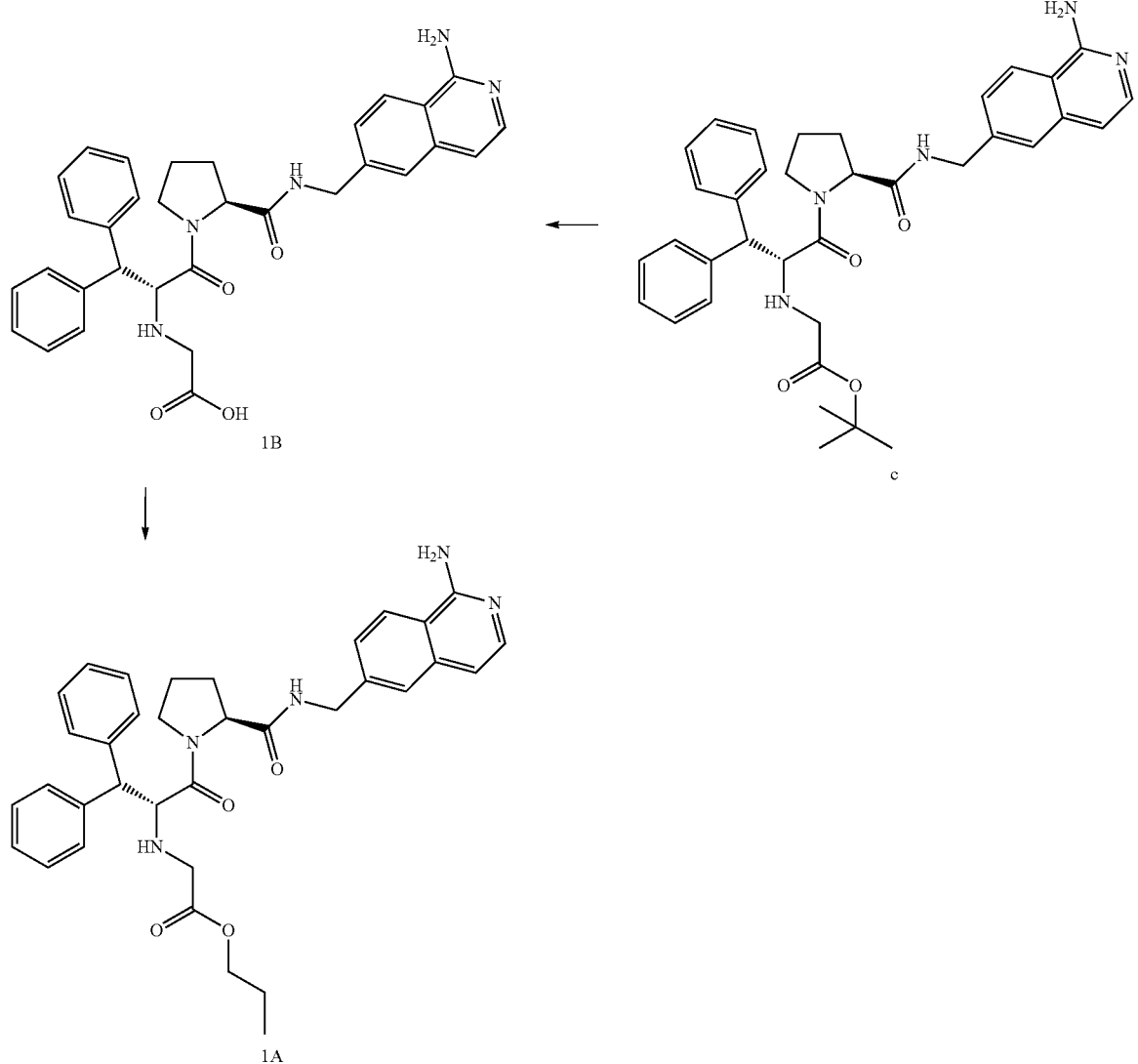

B: (S)-2-[[[(1-amino-6-isoquinolyl)methyl]amino]carbonyl]-1-pyrrolidine carboxylic acid 1,1-dimethylethyl ester hydrochloride (b)

To a stirred solution of N-tert-butoxycarbonyl-L-proline, Boc-Pro-OH, (6.73 g, 31.25 mmol) in anhydrous N,N-dimethylformamide (100 ml) under an argon atmosphere was added finely ground 1-amino-6-aminomethylisoquinoline hydrochloride (10.0 g, 40.63 mmol) and N,N-diisopropylethylamine (16.17 g, 125.00 mmol). After stirring the slurry for 15 minutes at room temperature 2-(1H-benzotriazole-1-yl)-1,1,3,3-tetramethyl-uronium hexafluorophosphate (17.67 g, 46.88 mmol) was added, portionwise, over 5 minutes, eventually resulting in complete dissolution of the suspended 1-amino-6-amino-methylisoquinoline hydrochloride. The reaction mixture was stirred at room temperature under an argon atmosphere for a further 90 minutes after which time a yellow precipitate of (S)-2-[[[(1-amino-6-isoquinolyl)methyl]amino]carbonyl]-1-pyrrolidine carboxylic acid 1,1-dimethylethyl ester hydrochloride (b) had formed. The precipitate was collected by filtration, washed with dichloromethane (300 ml) until the filtrate was colourless, and then dried under vacuum to give 7.8 g (56%) of title compound (94% pure by HPLC-Luna C18(2) 46×30 mm, gradient, mobile phase acetonitrile:water, 5-100%/4 min, constant 0.1% trifluoroacetic acid). Further product was isolated from the filtrate by evaporating under vacuum to remove dimethylformamide and excess diisopropylethyl amine and adding 500 ml dichloromethane. The resulting precipitate was removed by filtration, washed with dichloromethane (300 ml) and dried under vacuum to give 4.6 g (33%) (91% pure by HPLC-Luna C18 (2) 46×30 mm, gradient acetonitrile:water, 5-100%/4 min, constant 0.1% trifluoroacetic acid).

C: N-[2-(1,1-Dimethylethoxy)-2-oxoethyl]-β-phenyl-D-phenylalanyl-N-[(1-amino-6-isoqui-nolyl)methyl]-L-prolinamide hydrochloride (C)

To a suspension of (S)-2-[[[(1-amino-6-isoquinolyl)methyl]amino]carbonyl]-1-pyrrolidine carboxylic acid 1,1-dimethylethyl ester hydrochloride b (4.14 g, 9.34 mmol) in dichloromethane (20 ml) was added trifluoroacetic acid (8 ml). After stirring the solution for 2 hours the solvent and excess trifluoroacetic acid were removed in vacuo. The residue was then dissolved in N,N-dimethylformamide (41 ml) and 2-(tert-butyoxy-carbonylmethyl-amino)-3,3-diphenyl-propionic acid (Boc-D-Dpa-OH) (3.30 g, 9.3 mmol), 2-(1H-benzotriazole-1-yl)-1,1,3,3-tetramethyluronium hexafluorophosphate (5.31 g, 13.9 mmol) and N,N-diisopropylethylamine (9.75 ml, 56 mmol) were added. The mixture was stirred at room temperature for 1 hour then water added until a precipitate formed. The wet precipitate was collected by filtration then taken up in ethyl acetate, dried (MgSO$_4$), filtered and evaporated to dryness to give the crude product (7.2 g). Purification by column chromatography (silica, eluting gradient fashion with mixtures of dichloromethane and methanol (0-10%)) gave 4.6 g of the title compound c as a gum.

D: N-(carboxymethyl)-β-phenyl-D-phenylalanyl-N-[(1-amino-6-isoquinolyl)methyl]-L-pro-linamide hydrochloride (1B)

To a solution of N-[2-(1,1-dimethylethoxy)-2-oxoethyl]-β-phenyl-D-phenylalanyl-N-[(1-amino-6-isoquinolyl)methyl]-L-prolinamide hydrochloride c (4.6 g, 7.1 mmol) in dichloromethane (25 ml) was added trifluoroacetic acid (4.6 ml). After standing over-night the solution was evaporated to dryness, dissolved in dichloromethane and excess hydrochloric acid in diethyl ether added. The product was precipitated by addition of anhydrous diethyl ether then collected by filtration and dried under vacuum to give 2.8 g. A further 0.8 g was obtained by precipitation from the mother liquors.

$^1$H NMR δ(CD$_3$OD) 1.32 (m, 1H), 1.83 (m, 3H), 2.86 (m, 1H), 3.53 (m, 1H), 3.68 (dd, 2H; J=17.1 Hz), 3.80 (d, 2H; J=17.1 Hz) (4.15 (m, 1H), 4.52 (d, 1H; J=16.6 Hz), 4.59 (d, 1H; J=11.5 Hz), 4.69 (d, 1H; J=16.1 Hz), 5.3 (d, 1H, 11.5 Hz), 7.2-7.6 (m, 10H), 7.66 (d, 2H; J=7.5 Hz), 7.72 (dd, 1H; J=1.5, 8.0 Hz), 7.89 (s, 1H), 8.38 (d, 1H; J=9 Hz);
MS m/z 552.2 (M+H)+

E: N-(2-propoxy-2-oxoethyl)-β-phenyl-D-phenylalanyl-N-[(1-amino-6-isoquinolyl)methyl]-L-prolinamide dihydrochloride (1A)

To a suspension of N-(carboxymethyl)-β-phenyl-D-phenylalanyl-N-[(1-amino-6-isoquinolyl)methyl]-L-prolinamide hydrochloride (1B; 300 mg. 0.5 mmol) in n-propanol (5 ml) was added dropwise thionyl chloride (0.4 ml). After stirring for 3 days the solution was diluted with dichloromethane, washed with 5% aqueous sodium bicarbonate solution and evaporated to dryness. The crude product was purified by reverse phase HPLC and then converted to the hydrochloride salt by dissolving in a small amount of methanol and precipitating with 1M hydrochloric acid in diethyl ether. Following addition of further anhydrous diethyl ether the resulting precipitate was collected by filtration and dried under vacuum to give 185 mg of the title compound as a white powder.

$^1$H NMR δ(CD$_3$OD) 0.85 (t, 3H; J=7.5 Hz), 1.33 (m, 1H), 1.57 (sext, 2H; J=7 Hz), 1.83 (m, 3H), 2.88 (m, 1H), 3.51 (m, 1H), 3.73 (d, 1H; J=17.6 Hz), 3.84 (d, 1H; J=17.6 Hz), 4.07 (m, 2H), 4.16 (dd, 1H; J=5.0, 8.0 Hz), 4.53 (d, 1H; J=16.6 Hz), 4.56 (d, 1H; J=13.6 Hz), 4.70 (d, 1H; J=16.6 Hz), 5.20 (d, 1H; J=11 Hz), 7.23-7.44 (m, 7H), 7.50 (t, 2H; J=7.5 Hz), 7.56 (d, 1H; J=7.0 Hz), 7.65 (d, 2H; J=7.5 Hz), 7.72 (dd, 1H; J=1.5, 8.0 Hz), 7.90 (s, 1H), 8.39 (d, 1H; J=8.5 Hz); MS m/z 594.4 (M+H)+

Using methods similar to those described above and depicted in Scheme I corresponding derivatives were prepared starting from D-phenylalanine or O-methyl-D-tyrosine instead of D-diphenylalanine. Compounds 2B and 3B were isolated and used for subsequent testing as trifluoroacetate salts.

Example 2

2B: N-(carboxymethyl)-D-phenylalanyl-N-[(1-amino-6-isoquinolyl)methyl]-L-prolinamide trifluoroacetate

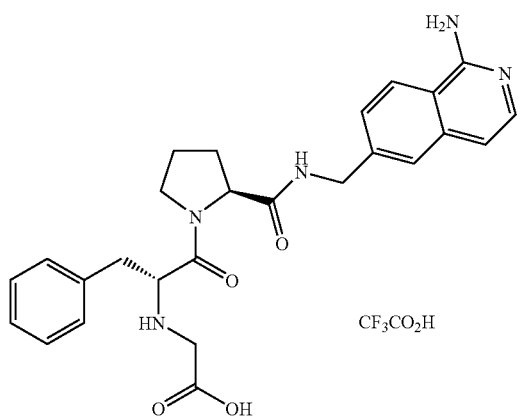

2B $^1$H NMR δ(CD$_3$OD) 1.41 (m, 1H), 1.85 (m, 2H), 1.99 (m, 1H), 2.47 (m, 1H), 3.35 (dd, 1H; J=5.0, 13.1 Hz), 3.40 (dd, 1H; J=10.6, 13.1 Hz), 3.45 (m, 1H), 3.73 (d, 1H; J=16.6 Hz), 3.80 (d, 1H; J=16.6 Hz), 4.34 (dd, 1H; J=4.5, 8.1 Hz), 4.5 (dd, 1H; J=5.0, 10.6 Hz), 4.51 (d, 1H; J=16.1 Hz), 4.72 (d, 1H; J=16.6 Hz), 7.23 (d, 1H; J=7.1 Hz), 7.27-7.43 (m, 5H), 7.52 (d, 1H; J=7.1 Hz), 7.71 (dd, 1H; J=1.5, 8.6 Hz), 7.90 (s, 1H), 8.34 (d, 1H; J=8.6 Hz); MS m/z 476.0 (M+H)+

2A: N-(2-propoxy-2-oxoethyl)-D-phenylalanyl-N-[(1-amino-6-isoquinolyl)methyl]-L-prolinamide hydrochloride

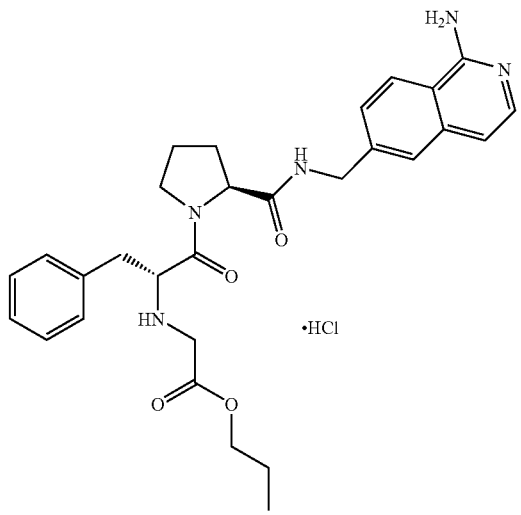

2A $^1$H NMR δ(CD$_3$OD) 0.89 (t, 3H; J=7.6 Hz), 1.41 (m, 1H), 1.62 (sext, 2H: J=7.6 Hz), 1.83 (m, 2H), 2.00 (m, 1H), 2.44 (m, 1H), 3.16 (dd, 1H; J=1.5, 10.6 Hz), 3.37 (dd, 1H; J=5.5, 13.1 Hz), 3.47 (m, 1H), 3.93 (d, 1H; J=17.1 Hz), 4.06 (d, 1H; J=17.1 Hz), 4.14 (m, 2H), 4.36 (dd, 1H; 5.0, 9.1 Hz), 4.54 (m, 2H), 4.71 (d, 1H; J=17.1 Hz), 7.26 (d, 1H, 7.1 Hz), 7.29-7.44 (m, 5H), 7.56 (d, 1H; J=7.1 Hz), 7.73 (d, 1H; J=8.6 Hz), 7.92 (s, 1H), 8.38 (d, 1H; J=8.6 Hz); MS m/z 518.2 (M+H)$^+$

Example 3

3B. N-(carboxymethyl)-O-methyl-D-tyrosinyl-N-[(1-amino-6-isoquinolyl)methyl]-L-prolinamide trifluoroacetate

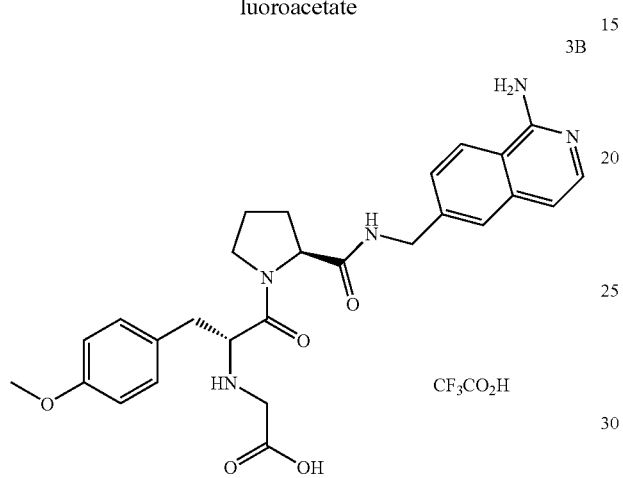

3B $^1$H NMR δ(CD$_3$OD) 1.46 (m, 1H), 1.87 (m, 2H), 2.02 (m, 1H), 2.56 (m, 1H), 3.08 (dd, 1H; J=10.6, 12.6 Hz), 3.27 (dd, 1H; J=5.5, 13.6 Hz), 3.47 (m, 1H), 3.71 (d, 1H; J=16.1 Hz), 3.79 (d, 1H; J=15.6 Hz), 3.79 (s, 3H), 4.36 (dd, 1H; J=4.0, 8.6 Hz), 4.46 (dd, 1H; J=4.0, 8.66 Hz), 4.51 (d, 1H; J=16.6 Hz), 4.72 (d, 1H; J=16.6 Hz), 6.92 (d, 2H; J=8.6 Hz), 7.21 (d, 2H; J=8.6 Hz), 7.24 (d, 1H, 7.1 Hz), 7.52 (d, 1H; J=7.1 Hz), 7.71 (d, 1H; J=8.1 Hz), 7.90 (s, 1H), 8.35 (d, 1H; J=9.1 Hz); MS m/z 506.3 (M+H)$^+$

3A: N-(2-propoxy-2-oxoethyl)-O-methyl-D-tyrosinyl-N-[(1-amino-6-isoquinolyl)methyl]-L-prolinamide hydrochloride

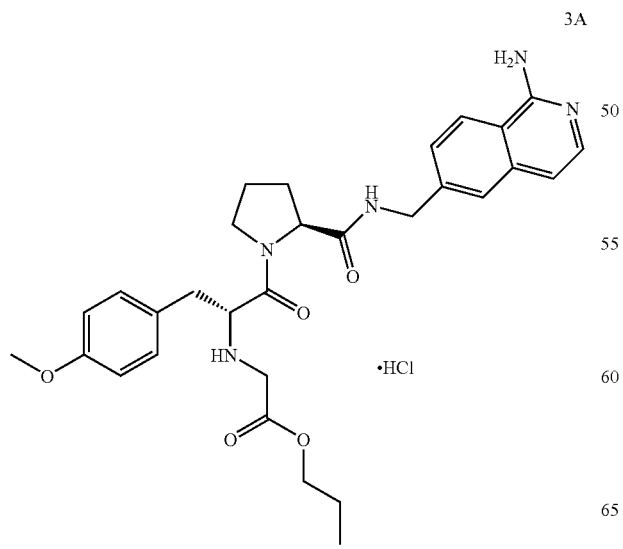

3A $^1$H NMR δ(CD$_3$OD) 0.88 (t, 3H; J=7.1 Hz), 1.47 (m, 1H), 1.61 (sext, 2H: J=7.1 Hz), 1.86 (m, 2H), 2.04 (m, 1H), 2.54 (m, 1H), 3.10 (dd, 1H; J=10.6, 15.1 Hz), 3.31 (m, 1H), 3.49 (m, 1H), 3.79 (s, 1H), 3.91 (d, 1H; J=16.6 Hz), 4.04 (d, 1H; J=16.6 Hz), 4.13 (m, 2H), 4.38 (dd, 1H; 5.0, 9.1 Hz), 4.48 (dd, 1H; J=5.0, 10.6 Hz), 4.54 (d, 1H; J=16.1 Hz), 4.71 (d, 1H; J=16.1 Hz), 6.93 (d, 2H; J=8.6 Hz), 7.22 (d, 2H; J=8.6 Hz), 7.26 (d, 1H, 7.1 Hz), 7.55 (d, 1H; J=7.1 Hz), 7.73 (dd, 1H; J=2.0, 8.6 Hz), 7.92 (s, 1H), 8.38 (d, 1H; J=8.6 Hz); MS m/z 548.3 (M+H)$^+$

Example 4

Assay of Thrombin Activity

Thrombin inhibitory activity was assessed by pre-incubating the test compound at a variety of concentrations with human α-thrombin at 37° C. After 10 min, the chromogenic substrate H-D-Phe-Pipecolinyl-Arg-ρ-nitroanilide (S-2238) was added to the mixture and the change in absorbance measured over the following 8 min. Both 1A and 1B were effective inhibitors of human α-thrombin in a concentration-dependent manner, with IC$_{50}$ values of 13.0 nM and 12.6 nM respectively (both n=5; FIG. 1). In further experiments in which the concentration of S-2238 was also varied, plots of [S]/V versus [S] were parallel for each concentration of S-2238 used indicating the competitive nature of the inhibition. Hanes-Woolf analysis of these data provided Ki determinations of 0.9 nM (n=5) for 1B and 1.0 nM (n=3) for 1A. A comparison with the activity parameters of compounds 2 and 3 are given in Table 1.

TABLE 1

| Thrombin inhibitory activity parameters | | |
|---|---|---|
| Compound | IC$_{50}$ (nM) | Ki (nM) |
| 1A | 13.0 | 1.0 |
| 1B | 12.6 | 0.9 |
| 2A | 573 | 34.5 |
| 2B | 864 | 45.5 |
| 3A | 197 | 1.8 |
| 3B | 358 | 5.4 |

Example 5

Determination of Bioavailability of Compounds 1A, 2A and 3A in Rats

Animals

Male Wistar Ola rats (~250 g). Food and water were available ad libitum throughout the studies.

Surgical Preparation

For intravenous pharmacokinetic studies, catheters (Portex polythene—ID 0.58 mm, OD 0.96 mm with a tip made from SF Medical silicone tubing, SFM1-1350) were inserted into the right jugular vein under isoflurane anaesthesia. The tubing was exteriorised at the back of the neck, filled with heparinised saline (100 Um/ml) and stoppered. Animals were allowed a minimum of 48 h recovery before dosing.

Administration of Compounds

Compounds 1A, 2A and 3A were administered orally (PO). Compounds 1B, 2B and 3B were administered intravenously (IV). Serial blood samples (for plasma) were taken from a lateral vein at points from 3 min to 24 hrs (terminal sample by cardiac puncture) according to a matrix design protocol (3 samples per time point). Plasma samples were stored at −20° C. until analysis.

Plasma Sample Analysis

Plasma samples were analyzed for the pertinent free acid thrombin derivatives 1B, 2B and 3B using an LC-MS method. Cmax (maximum plasma concentrations) and AUC values were determined from the mean plasma concentration—time profiles.

Compound 3A in saline was administered orally to 4 rats at 10 mg/kg base (2 mg/ml solution dosed at 5 ml/kg).

Results

Noncompartmental pharmacokinetic analysis was performed using WinNonlin Professional 3.1 and 4.1. The resulting pharmacokinetic parameters are presented in Table 2.

The bioavailability, expressed as AUC(IV)/AUC(PO)×100%, was found to be very high (58%) for the n-propylester derivative (1A) of the diphenylalanine derivative N-(carboxymethyl)-β-phenyl-D-phenylalanyl-N-[(1-amino-6-isoquinolyl)methyl]-L-prolinamide hydrochloride (1B) in comparison with the bioavailabilities of the corresponding phenylalanine (2A) and p-methoxyphenylalanine (3A) thrombin inhibitors.

TABLE 2

| | Pharmacokinetic parameters | | | | | | |
|---|---|---|---|---|---|---|---|
| Compound | $1B^a$ | $1B^b$ | $1B^b$ following administration of 1A | 2B | 2B following administration of 2A | 3B | 3B following administration of 3A |
| Dose (mg/kg) | 5 | 10 | 10 | 2 | 10 | 2 | 10 |
| Route | IV | PO | PO | IV | PO | IV | PO |
| Vehicle | Saline | | mul/sal | saline | saline | saline | Saline |
| AUC (IV) (ng/ml · h) | 4864 | | | 659 | | 1008 | |
| T½ (h) | 0.32 | | | 0.61 | | 0.16 | |
| Clearance (ml/min/kg) | 17 | | | 54 | | 34 | |
| Vss (L/kg) | 0.48 | | | 2.4 | | 0.46 | |
| C max (ng/ml) | | 35 | 2130 | | 4 | | 62 |
| T max (h) | | 1.2 | 1 | | 0.067 | | 1.6 |
| AUC (PO) (ng/ml · h) | | 119 | 5647 | | ND | | 97 |
| Bioavailability (%) | | 1.3 | $58^b$ | | Negligible | | 1.9 |

ND = not determined $^a$= data is a mean of two studies $^b$= the bioavailability of 1B following administration of 1A ranged between 30 and 60%, as measured in a number of experiments in Ola Wistar rats differing in the type of vehicle (suspension in gelatine/mannitol or a solution in mannitol/phosphate buffered saline or in 5% mulgofen/95% saline) used for compound 1A.

Experiments

The following sets of experiments were carried out:
  Compound 1B in saline was administered intravenously (IV) to 5 rats at 5 mg/kg base (5 mg/ml solution dosed at 1 ml/kg).
  Compound 1B in saline was administered orally (PO) to 4 rats at 10 mg/kg base (2 mg/ml solution dosed at 5 ml/kg).
  Compound 1A in 5% mulgofen/95% saline was administered orally to 5 rats at 10 mg/kg base (2 mg/ml solution dosed at 5 ml/kg).
  Compound 2B in saline was administered intravenously to 4 rats at 2 mg/kg base (2 mg/kg dosed at 1 ml/kg).
  Compound 2A in saline was administered orally to 4 rats at 10 mg/kg base (2 mg/ml solution dosed at 5 ml/kg).
  Compound 3B in saline was administered intravenously to 4 rats at 2 mg/kg base (2 mg/ml solution dosed at 1 ml/kg).

What is claimed is:

1. The compound N-(2-oxo-2-propoxyethyl)-β-phenyl-D-phenylalanyl-N-[(1-amino-6-isoquinolinyl)methyl]-L-prolinamide or a pharmaceutically acceptable salt thereof.

2. The compound of claim 1 as the dihydrochloride salt.

3. A pharmaceutical composition comprising the compound of claim 1 and a pharmaceutically acceptable carrier.

4. A method for treating a thrombin mediated disease in a subject in need thereof, the method comprising orally administering to the subject in need thereof an effective amount of the compound according to claim 1.

5. The compound N-(carboxymethyl)-β-phenyl-D-phenylalanyl-N-[(1-amino-6-isoquinolinyl)methyl]-L-prolinamide or a pharmaceutically acceptable salt thereof.

* * * * *